United States Patent [19]

Batt

[11] Patent Number: 5,093,351
[45] Date of Patent: Mar. 3, 1992

[54] SUBSTITUTED INDOLE, BENZOFURAN AND BENZOTHIOPHENE DERIVATIVES AS 5-LIPOXYGENASE INHIBITORS

[75] Inventor: Douglas G. Batt, Wilmington, Del.

[73] Assignee: Du Pont Merck Pharmaceutical Company, Wilmington, Del.

[21] Appl. No.: 293,522

[22] Filed: Jan. 5, 1989

[51] Int. Cl.$^5$ .................... A01N 43/38; A61K 31/40; C07D 209/04
[52] U.S. Cl. ................................. 514/415; 548/510; 548/469
[58] Field of Search ................. 514/415; 548/510, 469

[56] References Cited

U.S. PATENT DOCUMENTS 4,428,962  1/1984  Bristol .................. 548/469

FOREIGN PATENT DOCUMENTS 1180767  8/1986  Japan .
0186485  10/1966  U.S.S.R. .
1211030  11/1970  United Kingdom .

Primary Examiner—Robert A. Wax

[57] ABSTRACT

Provided are substituted indoles, benzofurans, and benzothiophenes of the formula

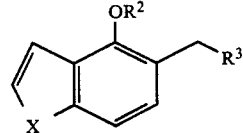

wherein X, $R^2$ and $R^3$ are described in the specification. These compounds are 5-lipoxygenase inhibitors and are useful as antiinflammatory agents.

18 Claims, No Drawings

SUBSTITUTED INDOLE, BENZOFURAN AND BENZOTHIOPHENE DERIVATIVES AS 5-LIPOXYGENASE INHIBITORS

BACKGROUND OF THE INVENTION

1. Field of Invention

This invention relates to substituted indole, benzofuran and benzothiophene derivatives, processes for their preparation, pharmaceutical compositions containing them, and methods of using them as 5-lipoxygenase inhibitors.

2. Background

The leukotrienes are oxidized polyunsaturated fatty acids which posses a multitude of biological activities. They are biosynthesized from arachidonic acid by the enzyme 5-lipoxygenase, which forms an unstable epoxide intermediate leukotriene $A_4$ ($LTA_4$). Further enzymatic action on this intermediate gives rise to two general classes of leukotrienes. The first class is represented by leukotriene $B_4$ ($LTB_4$). These compounds are chemotactic for inflammatory cells such as polymorphonuclear leukocytes, and cause degranulation and aggregation of inflammatory cells. They also increase vascular permeability, which leads to edema formation. A second class of leukotrienes, $LTC_4$, $LTD_4$, and $LTE_4$, are formed from $LTA_4$ by the addition of glutathione to the epoxide, and by further metabolic alterations of the peptide portion. These compounds are the major components of slow-reacting substance of anaphylaxis, and have been implicated in immediate hypersensitivity reactions. They can cause, among other effects, the contraction of smooth muscle, increases in mucus secretion, and increased vascular permeability. Many literature reviews are available discussing the biosynthesis and biological activities of the leukotrienes. Examples are Ford-Hutchinson, *ISI Atlas of Science: Pharmacology* (1987) 1, 25; Parker, *Ann. Rev. Immunol.* (1987) 5, 65; Needleman et al., *Ann. Rev. Biochem.* (1986) 55, 69; Sirois, *Advan. Lipid Res.* (1985) 21, 79; and Kulkarni and Parale, *Drugs of Today* (1985) 21, 329.

Because of their many biological effects, the leukotrienes are involved in the pathology of numerous inflammatory diseases (Bray, *Agents Actions* (1986) 19, 87; and reviews cited above). Such diseases include psoriasis, contact dermatitis, and other skin diseases (Greaves, in *Leukotrienes: Their Biological Significance*, P. J. Piper, ed; Raven (1986), p 175; Kragballe and Voorhees, *Acta Dermato-venereol.* (1985) suppl 120, 12), asthma and allergy (Lewis and Robin, *J Allergy Clin Immunol.* (1985) 76, 259), inflammatory bowel disease, ocular inflammation, arthritis, myocardial ischemia and circulatory shock (Lefer, *ISI Atlas of Science: Pharmacology* (1988) 2, 109). A therapeutic agent which effectively inhibits the biosynthesis of leukotrienes should be effective in the treatment of these and other inflammatory diseases where leukotrienes play a role (see, for example, Taylor and Clarke, *Trends Pharmacol Sci.* (1986) 7, 100; and Massicot et al., *Prostaglandins* (1986) 32, 481).

PRIOR ART 4-(Hydroxy or acyloxy)-5-substituted-indoles, -benzofurans, and -benzothiophenes, wherein the 5-substituent is methyl, aminomethyl, phenyl, or another substituent attached through carbon are known in the chemical literature. For example:

Moody, *J. Chem. Soc. Perkin Trans. I* (1984), 1333; El-Rayyes and Al-Salman, *J. Prakt. Chem.* (1976) 318, 816; Seemann et al., *Helv. Chim. Acta.* (1971) 54, 2411; Remers et al., *J. Org. Chem.* (1971) 36, 1232; Troxler et al., *Helv. Chim. Acta* (1968) 51, 1203; Brit. Pat. 1,211,030 Jpn. Kokai Tokkyo Koho JP 81,103,160 (*Chem. Abs.* 1982 96:6740v).

Suehiro and Eimura (*Bull. Chem. Soc. Japan* (1969) 42, 737) disclose 2-methyl-4-hydroxy-5,6-bis(phenylmethyl)indole as a chemical entity resulting from a dienone-phenol rearrangement of 5-oxo-2-methyl-4,4-bis(phenylmethyl)-3-ethoxycarbonyl-4,5-dihydroindole, followed by further chemical transformations.

None of the references cited above disclose activity of such compounds as inhibitors of leukotriene biosynthesis or as antiinflammatory agents.

European Patent Application 146,243 discloses 2-substituted benzothiophenes and benzofurans wherein the 2-substituent is or contains a carbonyl-containing functional group. These compounds are claimed to be 5-lipoxygenase inhibitors and/or leukotriene biosynthesis inhibitors.

European Patent Application 160,408 discloses 3-oxy-substituted-benzothiophene-2-carboxamides as lipoxygenase inhibitors.

European Patent Application 165,810 discloses 3-substituted benzothiophene and benzofuran derivatives as inhibitors of leukotriene biosynthesis.

European Patent Application 166,591 discloses 1-benzyl-2-carboxyalkylindole derivatives as inhibitors of leukotriene synthesis and antiinflammatory agents.

European Patent Application 187,487 discloses 3-substituted benzofurans and benzothiophenes which bear a 5-tetrazole or 5-tetrazolylaminocarbonyl substituent in the 2 position. These compounds are claimed as antiallergic and antiinflammatory agents.

European Patent Application 200,443 discloses 3-methyl-4-hydroxy-5-propyl-7-halo-benzofuran-2-carboxylate derivatives as lipoxygenase inhibitors, leukotriene biosynthesis inhibitors and antiinflammatories.

U.S. Pat. No. 4,737,519 discloses substituted naphthalenes, indoles, benzofurans, and benzothiophenes of the structure:

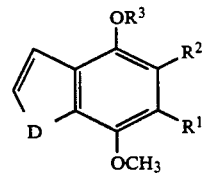

FIG. 1 wherein D is (CH=CH), $NCH_3$, S, or O; $R^1$ and $R^2$ are hydrogen, alkyl, alkenyl, and optionally substituted phenyl; and $R^3$ is hydrogen, acetyl, amino acyl, substituted benzoyl, or other substituted acyl; subject to a number of provisos. These compounds are disclosed as useful in the treatment of deepvein thrombosis and hypersecretion of mucus in the respiratory system. They are also reported to inhibit leukotriene production and/or 5-lipoxygenase.

None of the above-described references disclose the compounds of the present invention or suggest that such compounds would possess 5-lipoxygenase inhibitory activity or be antiinflammatory agents.

SUMMARY OF THE INVENTION

According to the present invention provided are compounds having the formula:

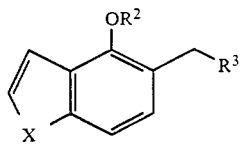

(I)

wherein
X is O, S, or NR[1];
R[1] is H, alkyl of 1-4 carbon atoms, or benzyl;
R[2] is H, or C(=O)R[4];
R[3] is pyridyl, 3,4-methylenedioxyphenyl, a 5-membered, aromatic heterocyclic ring with 1 or 2 heteroatoms selected independently from O, S, N or NR[8], with the proviso that if two heteroatoms are present then one must be N, and if only one is present it cannot be N; or phenyl optionally substituted with 1-3 groups each selected from F, Cl, Br, alkyl of 1-4 carbon atoms, alkoxy of 1-4 carbon atoms, thioalkyl of 1-4 carbon atoms, alkylsulfonyl of 1-4 carbon atoms, and NR[6]R[7];
R[4] is alkyl or alkoxy of 1-4 carbon atoms;
R[6] and R[7] independently are H or alkyl of 1-4 carbon atoms, or taken together are —(CH$_2$)$_4$—; and
R[8] is H or alkyl of 1-4 carbon atoms.

Also provided are pharmaceutical compositions containing compounds of Formula (I) and methods of using compounds of Formula (I) as 5-lipoxygenase inhibitors and as antiinflammatory agents.

Additionally provided are processes for preparing the compounds of Formula (I) as described hereinafter.

PREFERRED EMBODIMENTS

Preferred compounds are those compounds of Formula (I) where:
(a) X is NR[1]; and/or
(b) R[3] is phenyl; and/or
(c) R[2] is H or C(=O)CH$_3$.

Specifically preferred compounds are:
(a) 1-methyl-4-hydroxy-5-phenylmethyl indole.
(b) 1-methyl-4-acetoxy-5-phenylmethyl indole.

DETAILED DESCRIPTION OF THE INVENTION

Synthesis

The preparation of the compounds of the invention is described below, and is demonstrated by Examples 1 to 4.

Compounds of Formula (Ia), corresponding to compounds of Formula (I) wherein R[2] is H and X is O, S, or NR[1] (provided that R[1] is not hydrogen), may be synthesized using the method shown in Scheme A. Treatment of 4-oxo-4,5,6,7-tetrahydrobenzofuran (II, X=O), 4-oxo-4,5,6,7-tetrahydrobenzothiophene (II, X=S), or a 4-oxo-4,5,6,7-tetrahydroindole (II, X=NR[1]) with an aromatic aldehyde R[3]CHO in the presence of a strong base such as potassium t-butoxide in a solvent such as t-butanol, followed by treatment with a protic acid to protonate the resulting anion, provides the desired products. The reactions are carried out at temperatures between room temperature and the boiling point of the reaction solvent.

The starting cyclic ketones (II) are known in the chemical literature. For example, 4-oxo-4,5,6,7-tetrahydrobenzofuran and 4-oxo-4,5,6,7-tetrahydroindoles have been prepared by Matsumoto and Watanabe (*Heterocycles* (1984) 22, 2313), and Fieser and Kennelly (*J. Am. Chem. Soc.* (1935) 57, 1611) have reported the preparation of 4-oxo-4,5,6,7-tetrahydrobenzothiophene (IIc). Substituted benzaldehydes are either commercially available, or may be synthesized using any of a number of methods well known in the chemical literature.

Scheme A

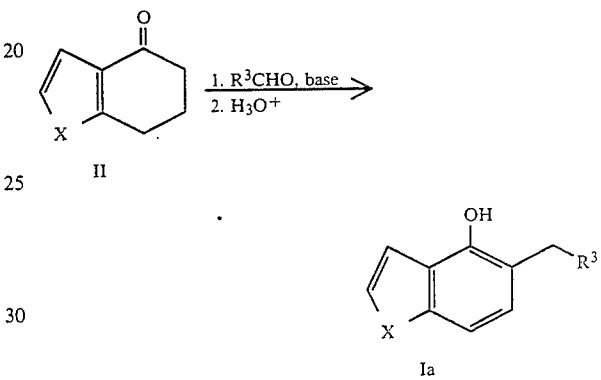

The preparation compounds of Formula (Ia) is demonstrated by Example 1.

Compounds of Formula (Ib), corresponding to compounds of Formula (I) wherein X is NH and R[2] is H, may be prepared using the method of Scheme B. Using the method of Henn, Hickey, Moody, and Rees (*J. Chem. Soc. Perkin Trans I*, (1984), 2189), a substituted benzaldehyde (III), wherein OP is a protected hydroxyl such as a benzyl ether or methyl ether, is treated with an alkali metal salt of an alkyl azidoacetate, such as the sodium salt of ethyl azidoacetate. This reaction is carried out in a suitable solvent such as ethanol, preferably at a temperature of between −20° and 0° C. The resulting substituted azidocinnamic acid ester (IV) is heated to a temperature of about 100° to 150° C. in a solvent such as toluene or xylene to provide (V). Substituted benzaldehydes of Formula (III) may be prepared using standard synthetic methods well known in the chemical literature.

The ester of (V) is saponified using standard reaction conditions, such as treatment with aqueous acid or base, to provide the corresponding carboxylic acid. The carboxylic acid is then decarboxylated using standard methods to provide the protected compound (VI). One such method involves heating the acid in a solvent such as quinoline with a catalyst such as metallic copper. Removal of the protecting group using appropriate known techniques then provides (Ib). For example, removal of a benzyl ether protecting group may be achieved by hydrogenation in a suitable solvent such as ethanol, in the presence of a catalyst such as palladium metal on an inert carbon support.

Scheme B

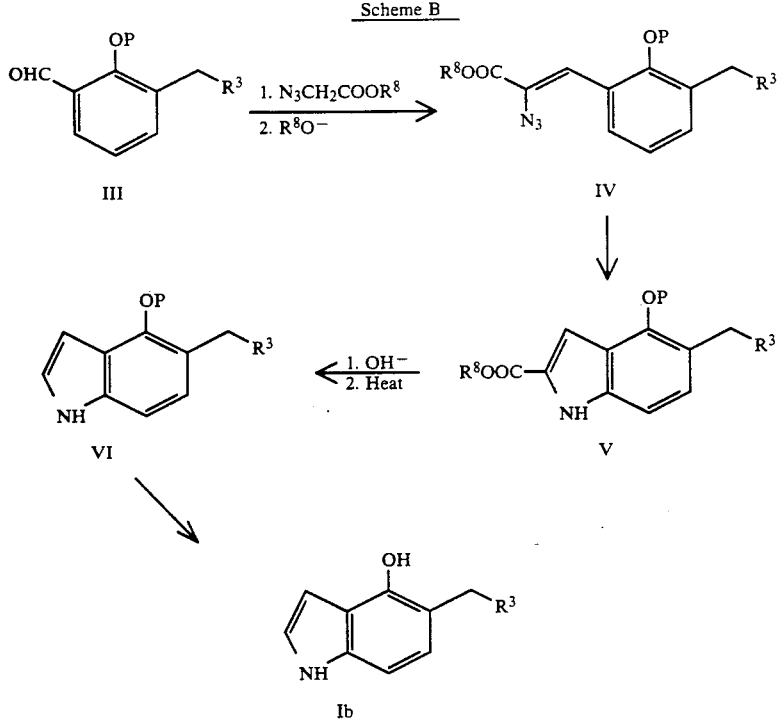

The synthesis of compounds of Formula (Ib) by this method is demonstrated in Example 2.

Compounds of Formula (Ic), corresponding to Formula (I) wherein X is $NR^1$ with $R^1$ other than H, and $R^2$ is H, may be prepared as shown in Scheme C. The intermediate compound of Formula (VI), which may be prepared as shown in Scheme B, is treated with a base such as sodium hydride or a sodium alkoxide, followed by an alkylating agent $R^1Y$ such as an alkyl halide or the alkyl ester of a sulfonic acid. These reactions are performed in a solvent such as an alcohol or tetrahydrofuran, and are generally performed at a temperature between about 0° C. and the boiling point of the solvent. The protecting group is then removed as previously described. This method is demonstrated by Example 3.

Scheme C

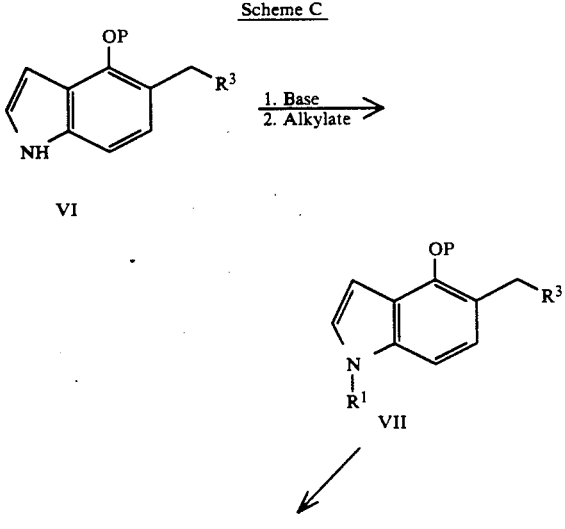

-continued
Scheme C

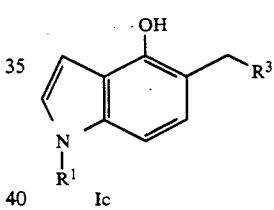

Compounds of Formula (Id), corresponding to compounds of Formula (I) wherein $R^2$ is not hydrogen, may be prepared from the corresponding compounds of Formula (Ia) as shown in Scheme D. This reaction is carried out by treatment of the starting material with an acylating agent such as an acid chloride $R^4COCl$ or an acid anhydride $(R^4CO)_2O$, in the presence of an amine base such as pyridine, 4-(N,N-dimethylaminopyridine), or triethylamine. These reactions may optionally be carried out in the presence of an inert solvent such as dichloromethane, or if the amine base is a liquid at room temperature, then the base may act as the reaction solvent. These reactions are carried out at a temperature between the freezing and boiling point of the solvent, preferably between about −15° C. and room temperature. Such acylation reactions are well known in the chemical literature. The preparation of these compounds is demonstrated by Example 4.

Scheme D

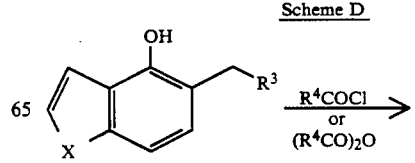

-continued
Scheme D

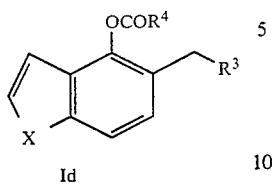

Id

The preparation of the compounds of the invention is described in greater detail in Examples 1 to 4. In these examples, all temperatures are in degrees Celsius. All reactions are performed under an atmosphere of dry nitrogen. Concentration under reduced pressure is performed with a rotary evaporator using a water aspirator. Flash chromatography refers to the method of medium-pressure column chromatography described by Still, Kahn and Mitra (*J. Org. Chem.* (1978) 43, 2923). The composition of solvent mixtures used as chromatographic eluents are given in percentages by volume. Nuclear magnetic resonance (NMR) spectra were obtained at a field strength of 200 mHz; abbreviations for NMR data are as follows: s=singlet, d=doublet, t=triplet, q=quartet, m=multiplet, CDCl$_3$=deuterochloroform solvent, DMSO-d$_6$=deutero-dimethylsulfoxide solvent. Peak positions for NMR data are reported as parts per million downfield from the internal standard tetramethylsilane. Infrared spectra were obtained as thin films (neat) or as finely-ground suspensions in mineral oil (mull); data are reported as peak positions in inverse centimeters. Abbreviations for mass spectra are: CI=methane chemical ionization; data are reported as the ratio of charge to mass of the parent ion.

EXAMPLE 1

Preparation of 1-Methyl-4-hydroxy-5-phenylmethylindole (Formula (I); X=NCH$_3$, R$^2$=H, R$^3$=phenyl).

A solution of 1-methyl-4-oxo-4,5,6,7-tetrahydroindole (Matsumoto and Watanabe, *Heterocycles* (1984) 22, 2313; 9.8 g, 0.066 mole) and benzaldehyde (7.0 g, 0.066 mole) in t-butanol (250 mL) was treated with potassium t-butoxide (14.7 g, 0.13 mole) and heated to reflux. After 18 hours, the mixture was cooled to room temperature and acidified with 1N hydrochloric acid. Most of the t-butanol was removed under reduced pressure, and the residue was extracted with dichloromethane. The organic phase was dried over magnesium sulfate, filtered, and concentrated under reduced pressure. The oily residue was flash chromatographed with 20% ethyl acetate in hexane to provide a pale yellow solid (9.3 g, 59%). This material was recrystallized from hexane/1-chlorobutane to provide white needles, mp 75°-77°. NMR (CDCl$_3$) 7.23 (m, 5H), 7.02 (d, J=7 Hz, 1H), 6.95 (d, J=3 Hz, 1H), 6.88 (d, J=7 Hz, 1H), 6.43 (d, J=3 Hz, 1H), 4.86 (s, 1H), 4.10 (s, 2H), 3.72 (s, 3H); IR (mull) 3340; Mass spec (CI) 238. Calculated for C$_{16}$H$_{15}$NO: C-80.97, H-6.37, N-5.90; found: C-80.78, H-6.32, N-5.81.

Representative compounds which were or can be prepared using the procedure of Example 1 are shown in Table 1.

TABLE 1

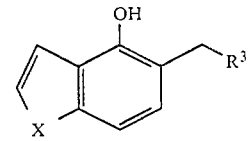

| Example | X | R$^3$ | Yield (%) | Melting Point (°C.) |
|---|---|---|---|---|
| 1a | NCH$_3$ | Ph | 59 | 76-77° |
| 1b | S | Ph | 19 | 82-83° |
| 1c | O | Ph | 10 | 84-86° |
| 1d | NCH$_2$Ph | Ph | 74 | 112-113° |
| 1e | NCH$_3$ | 4-CH$_3$O—Ph | 66 | 101-103° |
| 1f | NCH$_3$ | 3,4-(CH$_3$O)$_2$—Ph | 66 | 117-119° |
| 1g | NCH$_3$ | 3,4-(OCH$_2$O)—Ph | 36 | 133-135° |
| 1h | NCH$_3$ | 3-pyridyl | 9 | 201-203° |
| 1i | NCH$_3$ | 4-CH$_3$—Ph | 25 | 104-106° |
| 1j | NCH$_3$ | 4-F—Ph | 6 | 95-96° |
| 1k | NCH$_3$ | 4-Cl—Ph | | |
| 1l | NCH$_3$ | 3,4-Cl$_2$—Ph | | |
| 1m | NCH$_3$ | 3,4-F$_2$—Ph | | |
| 1n | NCH$_3$ | 4-CH$_3$S—Ph | | |
| 1o | NCH$_3$ | 4-(CH$_3$SO$_2$)—Ph | | |
| 1p | NCH$_3$ | 4-(CH$_3$)$_2$N—Ph | | |
| 1q | NCH$_3$ | 2-thienyl | 56 | Oil |

Ph = phenyl

EXAMPLE 2

Preparation of 4-hydroxy-5-phenylmethylindole (Formula (I); X=NH, R$^2$=H, R$^3$=phenyl.

Part A

2-Phenylmethoxy-3-phenylmethylbenzaldehyde.

Using the method of Tramposch, Kung and Blau (*J. Med. Chem.* (1983) 26, 121), 2-hydroxydiphenylmethane was converted to 3-(phenylmethyl)salicylaldehyde in 56% yield: NMR (CDCl$_3$) 11.35 (s, 1H), 9.35 (s, 1H), 7.45-6.85 (m, 8H), 4.00 (s, 2H); Mass spec (CI) 213. This hydroxyaldehyde (31.3 g, 0.147 mole) was treated with benzyl bromide (25.2 g, 0.147 mole) and potassium carbonate (22.1 g, 0.16 mole) in N,N-dimethylformamide (180 mL) at 100° overnight. After cooling to room temperature, the mixture was diluted with water and extracted with ethyl acetate. The organic phase was washed with water, dried over magnesium sulfate, filtered and concentrated under reduced pressure. Distillation of the residue (170°-185°, 0.1 torr) provided the title material as a pale yellow viscous oil in 71% yield. NMR (CDCl$_3$) 10.3 (s, 1H), 7.8-7.1 (m, 13H), 4.9 (s, 2H), 4.05 (s, 2H).

Part B

Ethyl 2-azido-2'-benzyloxy-3'-phenylmethylcinnamate. A solution of ethyl azidoacetate (54.0 g, 0.42 mole) and the product of Part A (35.8 g, 0.118 mole) in tetrahydrofuran (40 mL) was added dropwise to a stirred solution of sodium (11.7 g) in ethanol (300 mL) which was held at −5° to 0°. When addition was complete, the cold solution was stirred for 2 hours, then allowed to warm to room temperature. The mixture was poured into 2000 mL of water and extracted with ethyl acetate. The organic phase was washed with brine, dried over sodium sulfate, filtered and concentrated under reduced pressure. The residue was chromatographed with toluene, providing the title compound (35.0 g, 72%) as an oil. NMR (CDCl$_3$) 8.2-8.0 (m, 1H), 7.5-7.3 (m, 5H), 7.3-7.0 (m, 8H), 4.7 (s, 2H), 4.3 (q, 2H), 4.1 (s, 2H), 1.3 (t, 3H); Mass spec (CI) 414.

Part C

2-Ethoxycarbonyl-4-benzyloxy-5-phenylmethylindole. A solution of the product of Part B (35.0 g, 0.08 mole) in xylenes (400 mL) was added dropwise to 100 mL of boiling xylenes. After 3 hours, the reaction was cooled to room temperature, and the solvent removed under reduced pressure. The residue was recrystallized from toluene to provide the title compound as pale yellow crystals (22.5 g, 73%), mp 129°–131°. NMR (CDCl$_3$) 8.9 (broad s, 1H), 7.6–7.1 (m, 13H), 5.2 (s, 2H), 4.4 (q, 2H), 4.1 (s, 2H), 1.4 (t, 3H); Mass spec (CI) 386.

Part D

4-Benzyloxy-5-phenylmethylindole-1-carboxylic acid. A 1M solution (2 mL) of sodium hydroxide in water was added dropwise to a suspension of the product of Part C (4.0 g, 0.01 mole) in methanol (100 ml). When addition was complete, the mixture was heated to 50° for 18 hours, then allowed to cool to room temperature. The mixture was concentrated under reduced pressure, the residue slurried in 500 mL of hot water, and the pH adjusted to 1.0 with a 1N solution of HCl in water. The aqueous solution was extracted with methylene chloride. The organic phase was washed with water, dried over sodium sulfate, filtered, and concentrated under reduced pressure. Recrystallization of the residue from n-butyl chloride and a minimum amount of methanol provided the title compound as fluffy white crystals (3.02 g, 84.6%), mp 181°–183°. NMR (DMSO) 11.8 (broad s, 1H), 7.5–7.0 (m, 13H), 5.2 (s, 2H), 3.95 (s, 2H); mass spec (CI) 358.

Part E

4-Hydroxy-5-phenylmethylindole. A mixture of the product of Part D (11.0 g, 0.035 mole), copper bronze (2.2 g), and freshly distilled quinoline (165 mL) was vigorously degassed with nitrogen for 15 minutes. The mixture was quickly brought to reflux for 15 minutes while maintaining an inert atmosphere, then cooled to room temperature. The cooled solution was poured into 1N aqueous HCl and extracted with ethyl acetate. The organic phase was washed with 1N aqueous HCl, separated, dried over sodium sulfate, filtered through Celite ®, and concentrated under reduced pressure. The resulting oil was flash chromatographed with 5% hexane in toluene to provide in 45% yield a viscous oil which solidified on standing. Recrystallization from 1-chlorobutane/hexane provided the title product as fluffy white crystals (3.5 g, 36%), mp 104°–106°. NMR (CDCl$_3$) 8.75 (broad s, 1H), 7.5–7.1 (m, 12H), 7.0 (D, 1H), 6.65 (m, 1H), 5.2 (s, 1H), 4.1 (s, 1H); mass spec (CI) 314.

Part F

4-Hydroxy-5-phenylmethylindole. A solution of ethanol (50 mL) containing 10% palladium on carbon (0.25 g) and the product of Part E (1.7 g, 0.0054 mole) was hydrogenated under a gage pressure of 45 p.s.i. (3.1×10$^5$ Pa) of H$_2$ for 18 hours. The solution was filtered through Celite ® and the solvent removed under reduced pressure. The residue was recrystallized from 1-chlorobutane as white needles (1.0 g, 84%), mp 132°–134°. NMR (DMSO) 10.85 (broad s, 1H), 8.95 (broad s, 1H), 7.25–6.6 (m, 9H), 3.95 (s, 2H); IR (mull) 3539; Mass spec (CI) 224. Calculated for C$_{15}$H$_{13}$NO: C-80.69, H-5.87, N-6.27; Found: C-80.7, H-5.82, N-6.18.

Representative compounds which were or can prepared using the procedure of Example 2 are listed in Table 2.

TABLE 2

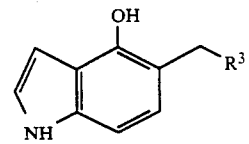

| Example | R$^3$ | Yield | Melting Point (°C.) |
|---------|-------|-------|---------------------|
| 2a | Ph | 84% | 132–134 |
| 2b | 4-F—Ph | | |
| 2c | 3-CH$_3$—Ph | | |

EXAMPLE 3

1-Ethyl-4-hydroxy-5-phenylmethylindole (Formula (I); X=NC$_2$H$_5$, R$^2$=H, R$^3$=phenyl).

Part A

4-Benzyloxy-5-phenylmethyl(N,ethyl)indole. A solution of the product of Example 2, Part E (1.75 g, 0.0055 mole) in tetrahydrofuran (THF) (10 mL) was added dropwise to a suspension of sodium hydride (0.17 g, 0.0072 mole) at −5°. The mixture was stirred for 30 minutes at room temperature then was added dropwise a solution of ethyl iodide (0.67 mL, 0.0083 mole) in THF (10 mL). The resulting solution was stirred at 45° for 18 hours under nitrogen. The solution was poured into water and extracted with ethyl acetate. The organic phase was washed with water, saturated aqueous sodium chloride, dried over magnesium sulfate, filtered, and the solvent removed under reduced pressure. The residue was twice flash chromatographed eluting with 20% ethyl acetate in hexane, then toluene. The title compound was obtained as a clear colorless oil (1.6 g, 83%). NMR (CDCl$_3$) 7.5–6.9 (m, 13H), 6.55 (D, 1H), 5.15 (s, 2H), 4.2–4.0 (m, 4H), 1.45 (T, 3H); mass spec 342.

Part B

1-Ethyl-4-hydroxy-5-phenylmethylindole. A solution of THF (50 mL) containing 10% palladium on carbon (0.25 g) and the product of Part A (1.6 g, 0.0046 mole) was hydrogenated under a gage pressure of 45 p.s.i. (3.1×10$^5$ Pa) of H$_2$ for 42 hours. The solution was filtered through Celite ® and the solvent removed under reduced pressure. The residue was flash chromatographed eluting with toluene. The title compound was obtained as a brown oil (0.7 g, 60%). NMR (DMSO) 9.0 (broad s, 1H), 7.35–7.05 (m, 6H) 6.85 (s, 2H), 6.6 (D, 1H), 4.1 (Q, 2H), 3.95 (s, 2H), 1.3 (t, 3H); Mass spec (CI) 252. Calculated for C$_{17}$H$_{17}$ON: C-81.24, H-6.82, N-5.57; found: C-80.89, H-7.00, N-5.43.

Representative compounds which were or can be prepared using the procedure of Example 3 are listed in Table 3.

TABLE 3

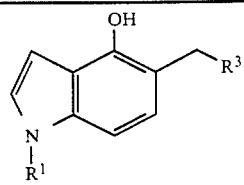

| Example | R¹ | R³ | Yield | Melting Point (°C.) |
|---------|-----|-----|-------|---------------------|
| 3a | C₂H₅ | Ph | 60% | (oil) |
| 3B | CH₂CH₂CH₃ | Ph | | |

EXAMPLE 4

Preparation of 1-Methyl-4-acetoxy-5-phenylmethylindole (Formula (I); X=NCH₃, R²=COCH₃, R³=phenyl).

A solution of the product of Example 1a (4.25 g, 0.018 mole) in pyridine (40 mL) was treated at 0° with acetic anhydride (2.74 g, 0.027 mole). The mixture was warmed to room temperature and stirred for 18 hours. After dilution with ethyl acetate, the pyridine was removed by washing with 1N hydrochloric acid until the wash water was acidic. The organic phase was then dried over magnesium sulfate, filtered, and concentrated under reduced pressure. The resulting oil was flash chromatographed with 20% ethyl acetate in hexane to provide in quantitative yield a viscous oil which slowly solidified. Recrystallization from 1-chlorobutane/hexane provided the title product as white needles (2.9 g, 58%), mp 56°–58°. NMR (CDCl₃) 7.4–7.2 (m, 6H) 7.03 (m, 2H) 6.28 (d, J=3, 1H), 4.00 (s, 2H) 3.23 (s, 3H) 2.30 (s, 3H); IR (mull) 1752; Mass spec (CI) 280. Calculated for C₁₈H₁₇NO₂: C-77.39, H-6.14, N-5.01; found: C-77.41, H-6.14, N-4.96.

Representative compounds which were or can be prepared using the procedure of Example 4 are shown in Table 4.

TABLE 4

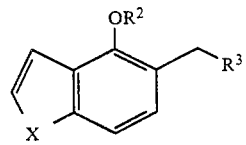

| Example | X | R² | R³ | Yield (%) | Melting Point (°C.) |
|---------|-----|------|------|-----------|---------------------|
| 6a | NCH₃ | COCH₃ | Ph | 58 | 56–58° |
| 6b | NCH₃ | COCH₃ | 2-thienyl | 32 | 84–86° |
| 6c | NCH₃ | COCH₃ | 4-CH₃O—Ph | 100 | (Oil) |
| 6d | NCH₃ | COCH₃ | 3,4-(CH₃O)₂—Ph | 64 | 92–94° |
| 6e | NCH₃ | COCH₃ | 4-CH₃—Ph | 88 | (Oil) |
| 6f | NCH₃ | COCH₃ | 3,4-(OCH₂O)—Ph | 62 | 112–113° |
| 6g | S | COCH₃ | Ph | | |
| 6h | O | COCH₃ | Ph | | |
| 6i | NCH₃ | COCH₂CH₃ | Ph | | |
| 6j | NCH₃ | COOCH₃ | Ph | | |
| 6k | NH | COCH₃ | Ph | 87 | (oil) |
| 6l | NCH₂CH₃ | COCH₃ | Ph | 89 | 69–71° |

PHARMACEUTICAL COMPOSITIONS

The compounds of the invention can be administered to treat inflammation, including but not limited to rheumatoid arthritis, osteoarthritis, psoriasis, contact dermatitis, allergy, asthma, and bronchitis, by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Compositions (dosage forms) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, spray, aerosol, liposome, or patch. Dosage forms used to administer the active ingredient usually contain suitable carriers, diluents, preservatives, or other excipients, as described in Remington's Pharmaceutical Sciences, A. Osol, a standard reference text in the field.

Gelatin capsules contain the active ingredient and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

The topical ointments, creams, gels, and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, isopropanol, ethyl carbonate, benzyl alcohol, propylene glycol, oils, glycerol, and fatty acid esters of sorbitol or mixtures thereof. Compositions for topical dosing may also contain preservatives or anti-oxidizing agents.

Powders and sprays can contain the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide, and a semipermeable membrane made from a suitable polymer to control the rate at which the material is delivered to the skin.

Useful pharmaceutical compositions for administration of the compounds of this invention can be illustrated as follows:

CAPSULES: A large number of unit capsules are prepared by filling standard two-piece hard gelatin capsules each with 50 mg of powdered active ingredient, 175 mg of lactose, 24 mg of talc, and 6 mg of magnesium stearate.

SOFT GELATIN CAPSULES: A mixture of active ingredient in soybean oil is prepared and injected by means of a positive displacement pump into gelatin to form soft gelatin capsules containing 50 mg of the active ingredient. The capsules are washed in petroleum ether and dried.

TABLETS: A large number of tablets are prepared by conventional procedures so that the dosage unit is 50 mg of active ingredient, 6 mg of magnesium stearate, 70 mg of microcrystalline cellulose, 11 mg of corn starch, and 225 mg of lactose. Appropriate coatings may be applied to increase palatability or delay absorption.

SUSPENSION: An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

INJECTABLE: A parenteral composition suitable for administration by injection is prepared by stirring 1.5% by weight of active ingredient in 10% by volume propylene glycol and water. The solution is sterilized by commonly used techniques.

NASAL SPRAY: An aqueous solution is prepared such that each 1 mL contains 10 mg of active ingredient, 1.8 mg methylparaben, 0.2 mg propylparaben and 10 mg methylcellulose. The solution is dispensed into 1 mL vials.

LUNG INHALER: A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

OINTMENT: The active ingredient is added to a mixture of 48% by weight white petrolatum, 10% liquid petrolatum, 8% glycerol monostearate, 3% isopropyl myristate, and 20% lanolin at 70° C. After thorough mixing, a warm solution of methyl and propyl parabens in water containing sodium acetone bisulfite is added such that the final concentrations of each paraben is 0.15%, of water is 8%, and of sodium acetone bisulfite is 0.5%.

The mixture is stirred until it has reached room temperature.

USE

The compounds of the invention have been shown to inhibit 5-lipoxygenase in an in vitro test system using rat basophilic leukemia (RBL-1) cells as the source of the enzyme. The test method is a modification of the procedure developed by Jakschik et al. (*Prostaglandins* (1978) 16, 733; *Biochem. Biophys. Res. Commun.* (1980) 95, 103; *Biochem. Biophys. Res. Commun.* (1981) 102, 624).

The 10,000×g supernatant from homogenized RBL-1 cells was incubated with test compound in a pH 7.0 phosphate buffer for five minutes. $^{14}$C-arachidonic acid was added to initiate the reaction, which was allowed to continue at 37° C. for two minutes. The reaction was stopped by freezing in a dry ice/ethanol slurry, and the 5-lipoxygenase products were separated from the substrate on silica gel columns. The amount of individual lipoxygenase products produced was determined and the percent inhibition calculated.

5-Lipoxygenase inhibitory activities for selected compounds of the invention are shown in Table 5.

TABLE 5

| Example | 5-lipoxygenase IC$_{50}$, μM |
|---|---|
| 1a | 0.056 |
| 1b | 0.13 |
| 1c | 0.40 |
| 1d | 0.042 |
| 6a | 0.42 |

The compounds of the invention were found to inhibit arachidonic acid-induced ear edema. This assay indicates a specific use in the treatment of skin diseases such as psoriasis. This assay also implies a reduction in leukotrienes caused by the compounds of the invention, and indicates the use of these compounds in other diseases where the production of leukotrienes is involved in the pathological process.

The assay is a modification of the procedure described by Young et al. (*J. Invest. Dermatol.* (1983) 80, 48). 1 mg of arachidonic acid is applied as an acetone solution to the inner surface of the pinna of CF1 mice. Test compound dissolved in acetone is applied to the ear just prior to the arachidonic acid challenge. One hour after challenge, 6 mm disks are removed from the ear with a biopsy punch, and the weight is determined. The results are determined as a percent inhibition of the swelling which occurs in the absence of the test compound.

Activities for selected compounds of the invention in the arachidonic acid ear edema assay are shown in Table 6.

TABLE 6

| Example | Arachidonic Acid Ear Edema % Inhibition at 100 μg/ear |
| --- | --- |
| 1a | 74 |
| 1b | 53 |
| 1c | 42 |
| 1d | 41 |
| 1e | 64 |
| 1g | 54 |
| 6a | 72 |
| 6b | 54 |
| 6c | 72 |

What is claimed is:

1. A compound having the formula:

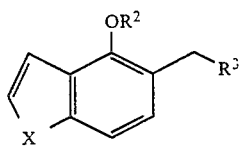

wherein
X is NR$^1$;
R$^1$ is an alkyl of 1-4 carbon atoms;
R$^2$ is H, or C(=O)R$^4$;
R$^3$ is phenyl optionally substituted with 1-3 groups each selected from F, Cl, Br, alkyl of 1-4 carbon atoms, alkoxy of 1-4 carbon atoms, thioalkyl of 1-4 carbon atoms, alkylsulfonyl of 1-4 carbon atoms, NR$^6$R$^7$ and 3,4-methylenedioxy;
R$^4$ is alkyl of 1-4 carbon atoms;
R$^6$ and R$^7$ independently are H or alkyl of 1-4 carbon atoms, or taken together are —(CH$_2$)$_4$.

2. A compound of claim 1 wherein R$^3$ is phenyl.
3. A compound of claim 1 wherein R$^2$ is H or

4. A compound of claim 1 wherein R$^3$ is phenyl and R$^2$ is H or

5. The compound of claim 1 which is 1-methyl-4-hydroxy-5-phenylmethyl indole.
6. The compound 1-methyl-4-acetoxy-5-phenylmethyl indole.
7. A pharmaceutical composition consisting essentially of a pharmaceutically acceptable carrier and a 5-lipoxygenase inhibiting amount of a compound of claim 1.
8. A pharmaceutical composition consisting essentially of a pharmaceutically acceptable carrier and a 5-lipoxygenase inhibiting amount of a compound of claim 2.
9. A pharmaceutical composition consisting essentially of a pharmaceutically acceptable carrier and a 5-lipoxygenase inhibiting amount of a compound of claim 3.
10. A pharmaceutical composition consisting essentially of a pharmaceutically acceptable carrier and a 5-lipoxygenase inhibiting amount of a compound of claim 4.
11. A pharmaceutical composition consisting essentially of a pharmaceutically acceptable carrier and a 5-lipoxygenase inhibiting amount of the compound of claim 5.
12. A pharmaceutical composition consisting essentially of a pharmaceutically acceptable carrier and a 5-lipoxygenase inhibiting amount of the compound of claim 6.
13. A method of inhibiting 5-lipoxygenase in a mammal comprising administering to the mammal an effective amount of a compound having the formula:

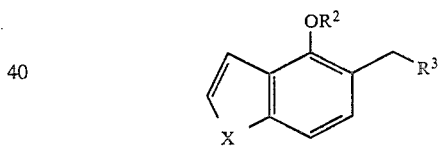

wherein
X is NR$^1$;
R$^1$ is H, alkyl of 1-4 carbon atoms, or benzyl;
R$^2$ is H, or C(=O)R$^4$;
R$^3$ is phenyl optionally substituted with 1-3 groups each selected from F, Cl, Br, alkyl of 1-4 carbon atoms, alkoxy of 1-4 carbon atoms, thioalkyl of 1-4 carbon atoms, alkylsulfonyl of 1-4 carbon atoms, NR$^6$R$^7$ and 3,4-methylenedioxy;
R$^4$ is alkyl or alkoxy of 1-4 carbon atoms;
R$^6$ and R$^7$ independently are H or alkyl of 1-4 carbon atoms, or taken together are —(CH$_2$)$_4$.

14. A method of claim 13 wherein R$^3$ is phenyl.
15. A method of claim 13 wherein R$^2$ is H or —C=OCH$_3$.
16. A method of claim 13 wherein R$^3$ is phenyl and R$^2$ is H or C=OCH$_3$.
17. A method of claim 13 wherein the compound is 1-methyl-4-hydroxy-5-phenylmethyl indole.
18. A method of claim 13 wherein the compound is 1-methyl-4-hydroxy-5-phenylmethyl indole.

* * * * *